United States Patent [19]

Baldwin et al.

[11] Patent Number: 4,675,321

[45] Date of Patent: Jun. 23, 1987

[54] SUBSTITUTED PYRIMIDINES USEFUL AS CALCIUM CHANNEL BLOCKERS

[75] Inventors: John J. Baldwin, Gwynedd Valley; Steven M. Pitzenberger; David E. McClure, both of Lansdale, all of Pa.

[73] Assignee: Merck & Co., Inc., Rahway, N.J.

[21] Appl. No.: 827,034

[22] Filed: Feb. 7, 1986

[51] Int. Cl.$^4$ .................. A61K 31/505; C07D 239/10; C07D 239/22

[52] U.S. Cl. .................................... 514/274; 544/122; 544/123; 544/316; 544/317; 544/318

[58] Field of Search ................. 514/274; 544/316, 318

[56] References Cited

U.S. PATENT DOCUMENTS

| | | | |
|---|---|---|---|
| 4,478,839 | 10/1984 | Benneche et al. | 514/274 |
| 4,582,834 | 4/1986 | Stenzel | 514/274 |
| 4,596,870 | 6/1986 | Benneche et al. | 544/316 X |

FOREIGN PATENT DOCUMENTS

| | | | |
|---|---|---|---|
| 0190974 | 10/1984 | Japan | 544/316 |
| 984365 | 2/1965 | United Kingdom | 544/316 |
| 2080301A | 2/1982 | United Kingdom | 514/274 |

OTHER PUBLICATIONS

Folkers, et al.; J.A.C.S., 54, (1932), pp. 3751–3758.
Folkers, et al.; J.A.C.S., 55, (1933), pp. 3784–3791.
C.A., 68, (1968), Ehsan, et al., 68:78231z.
C.A., 90, (1979), Elkasaby, 90:152115n.
Hillis; Journal of Cardiovascular Medicine, June 1980, pp. 583–587 and 590.
Naylor, et al.; Basic Research in Cardiology 76, (1981); pp. 1–15.
Berridge; Trends in Pharmacological Sciences, 1, (1980) pp. 419–424.
Khania, et al.; Khim Form. Zhurnal., 12(10), (1978) pp. 72–74.
Braunwald; The American Journal of Cardiology, 46, (1980), pp. 1045–1046.
Henry; The American Journal of Cardiology, 46, (1980), pp. 1047–1058.
Dangman, et al.; The American Journal of Cardiology, 46, (1980) pp. 1059–1067.

*Primary Examiner*—Joseph Paul Brust
*Attorney, Agent, or Firm*—Salvatore C. Mitri; Michael C. Sudol; Mario A. Monaco

[57] ABSTRACT

Pharmaceutical compositions of specific substituted pyrimidines and methods of treatment of certain cardiovascular disorders are disclosed. Also disclosed are novel substituted acrylated pyrimidines which are useful as calcium channel blockers.

9 Claims, No Drawings

SUBSTITUTED PYRIMIDINES USEFUL AS CALCIUM CHANNEL BLOCKERS

BACKGROUND OF THE INVENTION

The pharmacological function and importance of calcium antagonists, or calcium channel blockers, is well known and has been extensively reported in the literature [see; e.g., P. D. Henry, "Comparative Pharmacology of Calcium Antagonists: Nifedipine, Verapamil and Diltiazem", *The American Journal of Cardiology*, 46, 1047–1058 (1980); K. H. Dangman, et al, "Effects of Nifedipine on Electrical Activity of Cardiac Cells", *The American Journal of Cardiology*, 46, 1061–1067 (1980); E. Braunwald, "Introduction: Calcium Channel Blockers", *The American Journal of Cardiology*, 46,1045 (1980); L. D. Hillis, "The New Coronary Vasodilators: Calcium Blockers", *J. Card. Med.*, 5(6), 583 (1980); M. J. Berridge, "Receptors and Calcium Signalling", *Trends in Pharmacological Sciences* 1, 419, (1980); W. G. Nayler, et al, "Calcium Antagonists: definition and mode of action", *Basic Research in Cardiology*, 76, No. 1, 1–15 (1981)].

Non-acylated pyrimidines of the formula I below are disclosed by K. Folkers, et al, [*J. Am. Chem. Soc.*, 54, 3751–8 (1932)]; and K. Folkers and T. Johnson [*J. Am. Chem. Soc.*, 55, 3784–91 (1933)]; A. Ehsan and Karimulah [*Pakistan J. Sci. Ind. Res.*, 10(1), 83–5 (1967) (c.f. CA 68:78231z)]; and, E. L. Khania, et al, [*Khim. Farm. Zhurnal.*, 12(10), 72–4 (1978)]. Non-acylated tautomers of the pyrimidines of formula Ia below are disclosed by M. A. Elkasaby [*Pakistan J. Sci. Ind. Res.*, 21(2), 58–61 (1978) (c.f. CA 90: 152115n)].

SUMMARY OF THE INVENTION

This invention relates to pharmaceutical compositions of specific substituted pyrimidines and methods of treatment of certain cardiovascular disorders utilizing these pharmaceutical compositions.

This invention is also directed to novel substituted acylated pyrimidines and derivatives thereof and to methods for preparing such compounds.

DETAILED DESCRIPTION OF THE INVENTION

The novel substituted acylated pyrimidine compounds of this invention are represented by general structural formula (I) and the tautomers thereof (Ia):

wherein:
X is O or S;
R is COY wherein Y is $C_1$–$C_8$ alkyl, $C_2$–$C_8$ alkenyl, $C_3$–$C_8$ cycloalkyl, $C_1$–$C_8$ alkoxy, $C_2$–$C_8$ alkenyloxy, $C_3$–$C_8$ cycloalkyloxy, phenyl or —$NR^4R^5$ wherein $R^4$ and $R^5$ independently are hydrogen, $C_1$–$C_8$ alkyl, $C_7$–$C_{14}$ phenylalkyl or $R^4$ and $R^5$ together with the N atom form a 5 or 6 membered heterocycle selected from the group consisting of piperidinyl, morpholinyl, pyrrolidinyl, or $N'$-$C_1$-$C_4$-alkylpiperazinyl;

$R^1$ is aryl of 6 or 10 carbon atoms, substituted aryl with up to 5 substituents selected from $C_1$–$C_8$ alkyl, $C_1$–$C_8$ alkoxy, $C_1$–$C_8$ alkylthio, $C_1$–$C_8$ alkyl S(O), $C_1$–$C_8$ alkyl S(O)$_2$, $CF_3$, cyano, nitro, halo (i.e. fluoro, chloro or bromo), $CHF_2S$, $CH_2FS$ or $CONR^4R^5$ wherein $R^4$ and $R^5$ are as defined above, heteroaryl of 5 or 6 atoms containing up to four heteroatoms selected from O, S, or N, substituted heteroaryl with up to three substituents selected from $CF_3$, halo (F, Cl or Br), or $C_1$–$C_8$ alkylthio or benzoxadiazole;

$R^2$ is $C_1$–$C_8$ alkyl, $C_2$–$C_8$ alkenyl, $C_3$–$C_8$ cycloalkyl, $C_1$–$C_8$ hydroxyalkyl, $C_1$–$C_8$ dihydroxyalkyl, $C_2$–$C_8$ alkoxyalkyl, $C_3$–$C_8$ alkoxy(alkoxyalkyl), $C_1$–$C_8$ aminoalkyl wherein the amino group is $NR^4R^5$ in which $R^4$ and $R^5$ are as defined above or $R^2$ together with $R^3$ is methylene or ethylene;

$R^3$ is hydrogen, $C_1$–$C_8$ alkyl, $C_2$–$C_8$ alkenyl, $C_3$–$C_8$ cycloalkyl or $C_1$–$C_8$ hydroxyalkyl;

and pharmaceutically acceptable salts thereof.

The preferred compounds of this invention are those compounds represented by the general structural formulae (I) and the tautomers thereof (Ia) wherein:
X is O or S;
R is COY wherein Y is $C_1$–$C_8$ alkyl, $C_1$–$C_8$ alkoxy or $NR^4R^5$ in which $R^4$ is hydrogen or $C_1$–$C_8$ alkyl and $R^5$ is $C_7$–$C_{14}$ phenalkyl;
$R^1$ is aryl of 6 or 10 carbon atoms, substituted aryl wherein substituents are selected from $C_1$–$C_8$ alkyl, $C_1$–$C_8$ alkoxy, $C_1$–$C_8$ alkylthio, $CF_3$, cyano, nitro or halo or benzoxadiazole;
$R^2$ is $C_1$–$C_8$ alkyl, $C_2$–$C_8$ alkenyl or $C_1$–$C_8$ alkylamino wherein the amino group is $NR^4R^5$ in which $R^4$ is hydrogen or $C_1$–$C_8$ alkyl and $R^5$ is $C_7$–$C_{14}$ phenylalkyl; and
$R^3$ is hydrogen, $C_1$–$C_8$ alkyl, $C_2$–$C_8$ alkenyl or $C_3$–$C_8$ cycloalkyl.

The most preferred compounds of this invention are those compounds represented by the general structural formulae (I) and the tautomers thereof (Ia) wherein:
X is O or S;
R is COY wherein Y is $C_1$–$C_8$ alkyl or $C_1$–$C_8$ alkoxy;
$R^1$ is aryl of 6 carbon atoms or substituted aryl wherein substituents are selected from $C_1$–$C_8$ alkyl, $C_1$–$C_8$ alkoxy, $C_1$–$C_8$ alkylthio, $CF_3$, cyano, nitro or halo; and
$R^2$ and $R^3$ are $C_1$–$C_8$ alkyl.

Illustrative of these most preferred compounds are
(1) Ethyl 3-acetyl-6-methyl-4-(3-nitrophenyl)-3,4-dihydropyrimidine-2(1H)one-5-carboxylate [Formula (I) where X is O, R is acetyl, $R^1$ is 3-nitrophenyl, $R^2$ is ethyl and $R^3$ is methyl];
(2) Ethyl 3-acetyl-6-methyl-4-(3-nitrophenyl)-3,4-dihydropyrimidine-2(1H)thione-5-carboxylate [Formula (I) where X is S, R is acetyl, $R^1$ is 3-nitrophenyl, $R^2$ is ethyl and $R^3$ is methyl];
(3) Ethyl 3-acetyl-6-methyl-4-phenyl-3,4-dihydropyrimidine-2(1H)thione-5-carboxylate [Formula (I) where X is S, R is acetyl, $R^1$ is phenyl, $R^2$ is ethyl and $R^3$ is methyl;
(4) Ethyl 3-carbomethoxy-6-methyl-4-phenyl-3,4-dihydropyrimidine-2(1H)one-5-carboxylate [Formula (I) where X is O, R is —$CO_2CH_3$, $R^1$ is phenyl, $R^2$ is ethyl and $R^3$ is methyl];

(5) Ethyl 3-carbomethoxy-4-(2-methoxyphenyl)-6-methyl-3,4-dihydropyrimidine-2(1H)one-5-carboxylate [Formula (I) where X is O, R is —CO$_2$CH$_3$, R$^1$ is 2-methoxy-phenyl, R$^2$ is ethyl and R$^3$ is methyl]; and (6) Ethyl 3-carbomethoxy-6-methyl-4-(3-nitrophenyl)-3,4-dihydropyrimidine-2(1H)one-5-carboxylate [Formula (I) where X is O, R is —CO$_2$CH$_3$, R$^1$ is 3-nitrophenyl, R$_2$ is ethyl and R$^3$ is methyl].

Within the scope of this invention are pharmaceutical compositions useful in the treatment of cardiovascular disorders in which a high cellular concentration of Ca$^{++}$ a factor comprising a pharmaceutically acceptable carrier and a nontoxic therapeutically effective amount of a compound of formula (I) and the tautomers thereof (Ia) and pharmaceutically acceptable salts thereof.

The compounds of this invention are conveniently prepared from known or readily obtainable starting materials utilizing the general synthetic pathways described below:

The compounds of the formula (I) are prepared as follows:

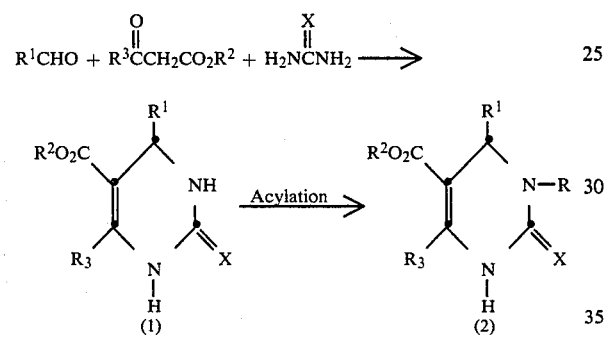

Utilizing the general procedures disclosed in the Folkers, et al or Ehsan et al references identified hereinabove, the appropriately substituted aldehyde, R$^1$CHO, is reacted with an appropriately substituted 3-oxopropanoate, such as ethyl acetoacetate, and urea or thiourea to give the dihydropyrimidine (1). The dihydropyrimidine (1) is then acylated by either treatment with a strong base and an acylating agent in an inert solvent or treatment with neat alkanoic acid anhydride at elevated temperatures. Examples of such strong bases include alkyl lithiums, such as methyl lithium, n-butyl lithium, and the like, metal hydrides such as sodium hydride and potassium hydride, and metal amides such as lithium diisopropylamide. Exemplifying the acylating agents are methyl chloroformate, ethyl chloroformate, dimethylcarbamyl chloride, diethylcarbamyl chloride, and the like. Illustrative of such alkanoic acid anhydrides are acetic anhydride, propionic acid anhydride and the like.

As indicated above, the compounds and compositions of this invention are useful as calcium entry blockers, and thus have broad pharmacological utility in that they exhibit (i) pronounced and long-lasting vasodilating effect accompanied by an energy-sparing effect on cardiac metabolism; (ii) antiarrythmic and antianginal action on cardiac muscle; (iii) vascular spasmolytic action; (iv) antihypertensive action; (v) spasmolytic action on the smooth muscle of the gastrointestinal and urogenital tracts and the cerebrovascular and respiratory systems; (vi) are useful antihypercholesterolemic and antilipidemic agents; (vii) protection of the ischemic myocardium; (viii) inhibit irritable bowel syndrome and esophageal spasm; and, (ix) inhibit migraine. Some of these compounds are also useful cardiotonic agents.

The representative compounds of the present invention were found to inhibit vascular calcium contraction, reduce cardiac contractile force, inhibit calcium-mediated tracheal contraction, inhibit calcium uptake in pituitary cells, or displace tritiated nitrendepine from membrane.

The compounds of the present invention can be administered in any suitable form; e.g. orally, sublingually, transdermally, or parenterally; i.e. intravenously, interperitoneally, etc. Thus, the compounds can be offered in a form (a) for oral administration e.q. as tablets in combination with other compounding ingredients customarily used such as talc, vegetable oils, polyols, benzyl alcohols, gums, gelatin, starches and other carriers; dissolved or dispersed or emulsified in a suitable liquid carrier; in capsules or encapsulated in a suitable encapsulating material; or (b) for sublingual administration; e.g., lactose tablets, and the like, for rapid dissolution or high molecular weight methylcellulose tablets, carboxymethylcellulose tablets, and the like, for slower, time-releasing delivery; or, (c) for parenteral administration e.g. dissolved or dispersed in a suitable liquid carrier or emulsified. The ratio of active compound to compounding ingredients i.e. carrier, diluent etc. will vary as the dosage form requires. Whatever form is used, the amount of compound of the present invention administered should be sufficient to achieve the pharmaceutical and/or therapeutic effect desired or required in the patient. Generally, doses of the compounds of the invention of from about 30 to about 3000 mg per day may be used, preferably about 100 to about 1000 mg per day. Dosages may be single or multiple depending on the daily total required and the unit dosage administered. Of course, the dose will vary depending upon the nature and severity of disease, weight of the patient, and other factors which a person skilled in the art will recognize.

It is often advantageous to administer compounds of this invention in combination with angiotensin converting enzyme inhibitors and/or antihypertensives and/or diuretics and/or β-blocking agents. For example, the compounds of this invention can be given in combination with such compounds as enalapril, hydralazine hydrochloride, hydrochlorothiazide, methyldopa, timolol, and the like, as well as admixtures and combinations thereof.

Typically, the individual daily dosages for these combinations can range from about one-fifth of the minimally recommended clinical dosages to the maximum recommended levels for the entities when they are given singly. Naturally, these dose ranges can be adjusted on a unit basis as necessary to permit divided daily dosages and, as noted above, can be varied depending on the nature and severity of the disease, weight of patient, special diets and other factors.

The following Examples are provided to further illustrate the best mode currently known for obtaining the compounds and the compositions of the invention, but are not to be construed as being limitative of the invention.

EXAMPLE 1

Preparation of Ethyl 3-acetyl-6-methyl-4-(3-nitrophenyl)-3,4-dihydropyrimidine-2(1H)one-5-carboxylate (a) Ethyl 4-(3-nitrophenyl)-3,4-dihydropyrimidine-2(1H)one-5-carboxylate (1a)

A mixture of urea (52 mmol), ethyl acetoacetate (78 mmol) and m-nitrobenzaldehyde (49 mmol) in absolute ethanol (30 mL) and concentrated hydrochloric acid (10 drop) was heated to reflux for 4.5 hours. Upon cooling to −20° C., a crude product crystallized. The crude product was recrystallized from isopropanol to afford the desired product as a white solid (m.p. 230.5°–233° C.).

(b) Ethyl 3-acetyl-6-methyl-4-(3-nitrophenyl)-3,4-dihydropyrimidine-2(1H)one-5-carboxylate Compound 1a (1.00 gr.) in acetic anhydride (25 mL) was heated to reflux for 45 minutes. The reaction mixture was cooled and concentrated in vacuo to give a tan solid. The tan solid was purified by flash chromatography on silica gel eluted with methanol:methylene chloride (2:98) and two recrystallizations from toluene to yield the desired product 1b (m.p. 190°–190.5° C.).

1H NMR(360 MHz,CDCl$_3$),δ=6.62 (S, 1H, ArC$\underline{H}$).

EXAMPLE 2

Preparation of Ethyl 3-acetyl-6-methyl-4-(3-nitrophenyl)-3,4-dihydropyrimidine-2(1H)thione-5-carboxylate (a) Ethyl 6-methyl-4-(3-nitrophenyl)-3,4-dihydropyrimidine-2(1H)thione-5-carboxylate (2a)

A mixture of m-nitrobenzaldehyde (3.02 g; 20 mmol), thiourea (1.52 g; 20 mmol), ethyl acetoacetate acetate (3.90 g; 30 mmol), concentrated hydrochloric acid (0.1 mL), and absolute ethanol (10 mL) was stirred and heated to reflux for 18 hr. The product crystallized after cooling to room temperature (5.1 g). Recrystallization from 95% ethanol gave pure pyrimidinethione as a white solid (3.6 g; 56%): mp=209°–10°; 1H NMR (d$_6$-DMSO, 360 MHz)δ=10.52 (s, 1H), 9.78 (br s, 1H), 8.18 (m, 1H), 8.09 (m, 1H), 7.69 (m, 2H), 5.35 (br s, 1H), 4.03 (q of q, 2H), 2.33 (s, 3H), 1.12 (t, 7Hz, 3H). Anal. Calcd. for C$_{14}$H$_{15}$N$_3$O$_4$S: C, 52.33; H, 4.70; N, 13.08. Found: C, 52.25; H, 4.64; N, 13.14.

(b) Ethyl 3-acetyl-6-methyl-4-(3-nitrophenyl)-3,4-dihydropyrimidine-2(1H)-thione-5-carboxylate Compound 2a (6.43 g; 20 mmol) was heated to reflux in acetic anhydride (50 mL) for 3 hr. A yellow solid (6.8 g, 94%) crystallized on cooling to room temperature. Traces of starting material were removed by chromatography on silica gel eluted with methanol:methylene chloride (1:99) and crystallization from acetonitrile to yield the desired product 2b: mp 213°–4.5°; 1H NMR (d$_6$-DMSO, 360 MHz)δ=11.78 (s, 1H), 8.17 (br d, 7 Hz, 1H), 8.03 (br s, 1H), 7.67 (m, 2H), 6.45 (s, 1H), 4.18 (q of q, 2H), 2.67 (s, 3H), 2.37 (s, 3H), 1.22 (t, 7 Hz, 3H). Anal. Calcd for C$_{16}$H$_{17}$N$_3$O$_5$S: C, 52.88; H, 4.72; N, 11.56. Found: C, 53.07; H, 4.80; N, 11.60.

EXAMPLE 3

Preparation of Ethyl 3-acetyl-6-methyl-4-phenyl-3,4-dihydropyrimidine-2(1H)thione-5-carboxylate Utilizing the general procedure of Example 2 and starting with benzaldehyde, thiourea and ethyl acetoacetate, ethyl 4-phenyl-3,4-dihydropyrimidine-2(1H)thione-5-carboxylate was prepared and then acylated with acetic anhydride to afford the title product as a solid (mp 142°–5° C.).

1H NMR (90 MHz, CDCl$_3$)δ=9.07(s,1H), 7.28(s,5H), 6.69(s,1H), 4.23(q,7 Hz,2H), 2.77(s,3H), 2.34(s,3H), 1.23(t,7 Hz,3H).

Anal. Calcd for C$_{16}$H$_{18}$N$_2$O$_3$S:
C, 60.36; H, 5.70; N, 8.80.
Found: C, 60.40; H, 5.88; N, 8.82.

EXAMPLE 4

Preparation of Ethyl 3-carbomethoxy-6-methyl-4-phenyl-3,4-dihydropyrimidine-2(1H)one-5-carboxylate To a suspension of ethyl-6-methyl-4-phenyl-3,4-dihydropyrimidine-2(1H)one-5-carboxylate (5.0 mmol) in dry tetrahydrofuran (b 10 mL) under nitrogen at −78° C. was added dropwise 1.5 M methyllithium (11 mmol) in diethyl ether and the reaction mixture allowed to warm to 25° C. After 30 minutes, the reaction mixture was recooled to −78° C. and methyl chloroformate (5.5 mmol) was added. The reaction mixture was allowed to warm to 25° C., then quenched with saturated aqueous ammonium chloride and extracted with methylene chloride. The combined organic extracts were dried over anhydrous sodium sulfate, filtered and the filtrate concentrated in vacuo. The residue was purified by flash chromatography on silica gel eluted with methanol:methylene chloride (5:95) and recrystallized from acetonitrile to give the title product as a solid (mp=179°–180.5° C.).

1H NMR (360 MHz, CDCl$_3$)δ=6.38 (S, 1H, ArC$\underline{H}$).

EXAMPLE 5

Preparation of Ethyl 3-carbomethoxy-4-(2-methoxy-phenyl)-6-methyl-3,4-dihydropyrimidine-2(1H)one-5-carboxylate Utilizing the general procedure of Example 4, ethyl 4-(2-methoxyphenyl)-3,4-dihydropyrimidine-2(1H)one-5-carboxylate was reacted with methyl chloroformate to give the title product as a solid (mp=147°–150° C.).

EXAMPLE 6

Preparation of Ethyl 3-carbomethoxy-6-methyl-4-(3-nitrophenyl)-3,4-dihydropyrimidine-2(1H)one-5-carboxylate Utilizing the general procedure of Example 4, ethyl 4-(3-nitrophenyl)-3,4-dihydropyrimidine-2(1H)one-5-carboxylate was reacted with methyl chloroformate to give the title product as a solid (mp=170°–173° C.).

EXAMPLES 7–12

The following compounds of the formula (I) where X is O are prepared from the appropriate starting materials utilizing the above described general procedures. (Me is methyl; Et is ethyl; Pr is propyl; φ is phenyl)

| Compound No. | R | R¹ | R² | R³ |
|---|---|---|---|---|
| 7 | COCH₃ | φ | Me | Me |
| 8 | COCH₃ | 2-Brφ | Pr | Me |
| 9 | COEt | 4-Meφ | —CH₂CH₂—N(CH₃)—CH₂φ | Et |
| 10 | CO₂Et | 2-MeSφ | —CH₂CH=CH₂ | —CH₂CH=CH₂ |
| 11 | CO₂Et | benzofurazanyl | Me | Me |
| 12 | CO₂Et | naphthyl | Et | Et |

EXAMPLES 13–19

The following compounds of formula (I) where X is S are prepared from the appropriate starting materials utilizing the above-described procedures. (Me is methyl; Et is ethyl; Pr is propyl; φ is phenyl)

| Compound No. | R | R¹ | R² | R³ |
|---|---|---|---|---|
| 13 | —CO₂CH₃ | φ | Me | Me |
| 14 | —COCH₃ | 2-MeOφ | Et | Et |
| 15 | —CO₂CH₃ | φF₅ | Et | Pr |
| 16 | —CO₂Et | 3-Meφ | Et | Me |
| 17 | —COCH₃ | naphthyl | Et | Me |
| 18 | —CO₂CH₃ | benzofurazanyl | —CH₂CH=CH₂ | —CH₂CH=CH₂ |
| 19 | —CO₂Et | 2,3-diClφ | Et | Me |

EXAMPLE 20

Ethyl 3-carbomethoxy-6-methyl-4-(3-nitrophenyl)-3,4-dihydropyrimidine-2(1H)one-5-carboxylate As specific embodiment of a composition of this invention an active ingredient, such as is formulated to yield 5000 compressed tablets, each containing 50 mg of the active ingredient, as follows:

| | |
|---|---|
| Active ingredient | 250 grams |
| Starch | 70 grams |
| Dibasic calcium phosphate hydrous | 500 grams |
| Calcium stearate | 2.5 grams |

What is claimed is:
1. A compound having structural formulae (I) and the tautomers thereof (Ia)

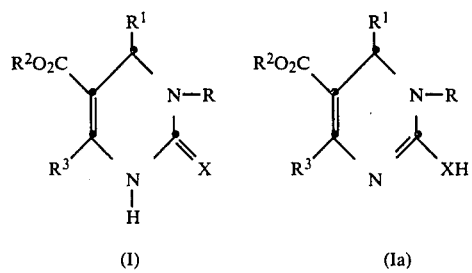

wherein:
- X is O or S;
- R is COY wherein Y is $C_1$–$C_8$ alkyl or $C_1$–$C_8$ alkoxy;
- $R^1$ is aryl of 6 carbon atoms or substituted aryl wherein substituents are selected from $C_1$–$C_8$ alkyl, $C_1$–$C_8$ alkoxy, $C_1$–$C_8$ alkylthio, $CF_3$, cyano, nitro or halo; and
- $R^2$ and $R^3$ are $C_1$–$C_8$ alkyl.

2. A compound according to claim 1 which is ethyl 3-acetyl-6-methyl-4-(3-nitrophenyl)-3,4-dihydropyrimidine-2(1H)one-5-carboxylate.

3. A compound according to claim 1 which is ethyl 3-acetyl-6-methyl-4-(3-nitrophenyl)-3,4-dihydropyrimidine-2(1H)thione-5-carboxylate.

4. A compound according to claim 1 which is ethyl 3-acetyl-6-methyl-4-phenyl-3,4-dihydropyrimidine-2(1H)thione-5-carboxylate.

5. A compound according to claim 1 which is ethyl 3-carbomethoxy-6-methyl-4-phenyl-3,4-dihydropyrimidine-2(1H)one-5-carboxylate.

6. A compound according to claim 1 which is ethyl 3-carbomethoxy-6-methyl-4-(2-methoxyphenyl)-3,4-dihydropyrimidine-2(1H)one-5-carboxylate.

7. A compound according to claim 1 which is ethyl 3-carbomethoxy-6-methyl-4-(3-nitrophenyl)-3,4-dihydropyrimidine-2(1H)one-5-carboxylate.

8. A pharmaceutical composition useful in the treatment of cardiovascular disorders in which a high cellular concentration of $Ca^{++}$ is a factor comprising a pharmaceutically acceptable carrier and a nontoxic $Ca^{++}$ controlling amount of a compound represented by general structural formulae (I) and the tautomers (Ia) thereof as defined in claim 1.

9. A method of treatment for cardiovascular disorders in which a high cellular concentration of $Ca^{++}$ is a factor which comprises administering to a subject in need of such treatment a non-toxic $Ca^{++}$ controlling amount of a compound of structural formulae (I) and the tautomers (Ia) thereof as defined in claim 1.

* * * * *